United States Patent
Tu (10) Patent No.: US 6,267,781 B1
(45) Date of Patent: Jul. 31, 2001

(54) MEDICAL DEVICE AND METHODS FOR TREATING VALVULAR ANNULUS

(75) Inventor: Hosheng Tu, Tustin, CA (US)

(73) Assignee: Quantum Therapeutics Corp., Dana Point, CA (US)

( * ) Notice: Subject to any disclaimer, the term of this patent is extended or adjusted under 35 U.S.C. 154(b) by 0 days.

(21) Appl. No.: 09/414,938

(22) Filed: Oct. 9, 1999

Related U.S. Application Data (63) Continuation-in-part of application No. 09/143,890, filed on Aug. 31, 1998, now Pat. No. 5,980,563.

(51) Int. Cl.$^7$ .................................................. A61F 7/12
(52) U.S. Cl. ........................ 607/113; 607/101; 607/102
(58) Field of Search .................... 607/96, 98, 99, 607/101–102, 113; 606/41, 42, 48–50

(56) References Cited

U.S. PATENT DOCUMENTS

| | | | |
|---|---|---|---|
| 5,249,585 | * 10/1993 | Turner et al. | 607/99 |
| 5,846,241 | * 12/1998 | Kittur et al. | 606/48 |
| 6,047,700 | * 4/2000 | Eggers et al. | 128/898 |
| 6,068,653 | * 5/2000 | LaFontaine | 607/116 |
| 6,083,219 | * 7/2000 | Laufer | 606/27 |

* cited by examiner

*Primary Examiner*—Roy Gibson (57) ABSTRACT

An ablation device for treating tissues, valvular annulus, valvular organ structure, or atherosclerosis of a patient, the ablation device including a flexible elongate tubular shaft having a deployable spiral wire electrode at its distal end adapted to contact/penetrate the tissue to be treated and to apply high frequency energy to the tissue for therapeutic purposes.

18 Claims, 6 Drawing Sheets

MEDICAL DEVICE AND METHODS FOR TREATING VALVULAR ANNULUS

CROSS-REFERENCE TO RELATED APPLICATIONS

This application is a continuation-in-part of application Ser. No. 09/143,890, filed Aug. 31, 1998 now U.S. Pat. No. 5,980,563 issued Nov. 9, 1999. The entire content is incorporated herein by reference.

FIELD OF THE INVENTION

The present invention generally relates to improved medical device and methods for treating cardiovascular tissues, and more particularly, to such an ablation device and methods for treating valvular annulus, atherosclerosis, or tissues in a patient by delivering therapeutic RF energy through an electrode to the specific lesion sites.

BACKGROUND OF THE INVENTION

An artery is one of the tube-shaped blood vessels that carry blood away from the heart to the body's tissues and organs. An artery is made up of outer fibrous layer, smooth muscle layer, connecting tissue and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or cells to the blood stream.

There are limitations, however, to this technique's application, depending on the extent of the disease, the blood flow through the artery, and the part of the anatomy and the particular vessels involved. Plaque build-up and/or severe re-stenosis recurs within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. The underlying fresh tissue or cells still pose as a precursor for vessel reclosures or angio-spasm.

When a clogged artery is widened, the plaque is broken up and the underlying collagen or damaged endothelium is exposed to the blood flow. Collagen has a prothrombotic property that is part of body healing process. Unless the collagen or the damaged endothelium is passivated or modulated, the chance for blood vessel clotting as well as restenosis exists. This same phenomenon occurs in the valvuloplasty where the valvular annulus is enlarged by a balloon, wherein collagen could be denuded and/or endothelium could be damaged. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, Aug. 1998). Therefore, it becomes imperative to post-treat walls after the walls are treated with angioplasty, stenting, and/or valvuloplasty procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment device have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the tissue site to obtain the desired temperature for treating a tissue.

The human's circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole. The pulmonary valve separates the right ventricle from the pulmonary artery. The mitral valve, so named because of its resemblance to a bishop's mitre, is in the left ventricle and it separates the left atrium from the ventricle. The fourth valve is the aortic valve that separates the left ventricle from the aorta. In a venous circulatory system, a venous valve is to prevent the venous blood from leaking back into the upstream side so that the venous blood can return to the heart and the lungs for blood oxygenating purposes.

In either the case of valvuloplasty or valvular dysfunction, the annular organ structure of a heart valve, a valve leaflet, a chordae tendinae, papillary muscles, a venous valve, and the like still needs to be treated and/or tightened so that the valvular function is competent. The current technology for valve repair or valve replacement requires an expensive open-heart surgery that needs a prolonged period of recovery. A less invasive catheter-based valve repair technology becomes an unmet clinical challenge.

Therefore, there is a clinical need to have a less invasive catheter-based approach for treating an annular organ structure of a heart valve, a venous valve, a valve leaflet, a chordae tendinae, papillary muscles, and the like by using high frequency energy for reducing and/or shrinking a tissue mass for tightening and stabilizing the dilated tissue adjacent a valvular annulus or an annular organ structure.

SUMMARY OF THE INVENTION

In general, it is an object of the present invention to provide a method and an improved medical ablation device for generating heat, to treat the atherosclerosis, vascular vessels, other tissues such as intestine, colon, ureter, uterine tube, and other annular organ structure of a heart valve, a venous valve, a valve leaflet, chordae tendinae, papillary muscles, and the like.

It is another object of the present invention to provide a method and a device for monitoring the temperature of the ablated tissue, and to control the temperature by utilizing a temperature control mechanism and/or algorithm. The location of the temperature sensor means is preferably at close proximity of the electrode means of the ablation device.

It is still another object of this invention to provide a method and an device for treating atherosclerosis, vascular walls, or tubular cellular tissues in a patient by applying high frequency current to a pre-implanted stent and consequently to the underlying tissues or to an electrode that could penetrate the tissue in order to tighten and stabilize the treated tissue.

Briefly, heat is generated by supplying a suitable energy source to a device, which is comprised of at least one electrode means, in contact with the body tissues through a pre-implanted stent or an electrode. A "pre-implanted stent" is defined in this invention as any metallic stenting element, in mesh form, coil form or other appropriate form, used to enlarge and maintain the enlarged tissues or vessels. Examples include coronary stent, peripheral stent, uterine stent and the like. A suitable energy source may consist of radiofrequency energy, microwave energy, ultrasonic energy, alternating current energy, or laser energy. The energy can be applied to the stent and consequently to the atherosclerosis, vascular walls, or cellular tissues of an annular organ structure through the electrode means. In a RF operating mode, a DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the high frequency energy delivered and by the delivery duration. The standard high frequency energy generator means and its applications through the electrode means, to a patient are well known for an ordinary artisan who is skilled in the art.

In an optional embodiment, means for generating vibration at the distal section comprises a motor mounted in the cavity of the handle, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the device vibrates.

In one embodiment, the device comprises a deployable wire electrode or plurality of wire electrodes. In a preferred embodiment, the wire electrode is a spiral wire electrode having at least one of the next spiral always larger than the prior spiral, so that resilience and semi-compressibility becomes the property of the wire electrode to ultimately deploy to its full extent. The deployed wire electrode is to intimately contact a pre-implanted stent at any contact point and subsequently the stent becomes an electrode means because the stent contacts the tissues behind itself. In another optional embodiment, the spiral wire electrode directly contacts a tissue for therapeutic purposes. The wire electrode is connected to an external high frequency current generating means through an electrical conductor. In the case of a wire electrode inside a tubular vessel, the wire electrode is preshaped and is extendable to its maximum distance radially to contact the pre-implanted stent or an inner wall of an annular organ structure. The wire electrode is semi-compressible so that when the deployed wire is pressed against the stent or a tissue, an appropriate pressure is exerted onto the stent or the tissue to ensure intimate contact when applying the high frequency energy therapy.

The method and medical device of the present invention has several significant advantages over other known systems or techniques to treat the atherosclerotic tissues having at least one pre-implanted stent or treat an annular organ structure of a valvular annulus, a heart valve, a venous valve, a valve leaflet, a chordae tendinae, papillary muscles and the like. In particular, the device system comprising the extendible wire electrode means, using RF energy as a heat source, in this invention and simultaneously applying pressure to the pre-implant stent or the tissue, results in a more efficient therapeutic effect, which is highly desirable in its intended application on the atherosclerosis or on other tissue ablation applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of the medical device system and methods, comprising applying high frequency energy to treat the atherosclerosis, vascular vessels, or other annular cellular tissues of a patient through a wire electrode of the present invention.

Figure 1:
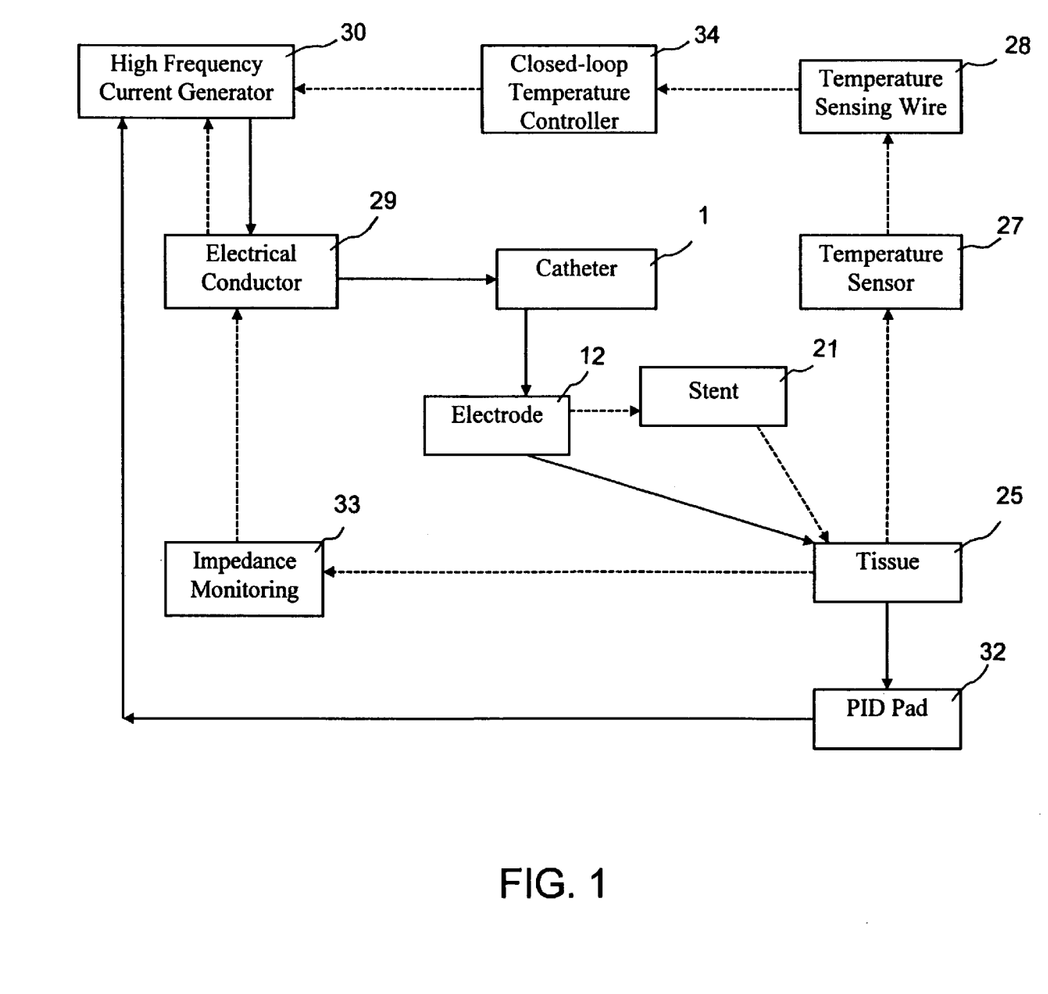
FIG. 1 is a schematic diagram of a high frequency treatment method in relation to the tissues or atherosclerosis through an electrode.

FIG. 1 shows a schematic diagram of a high frequency energy or RF energy treatment method in relation to the tissues or atherosclerosis through an optional pre-implanted metallic stent or to a tissue directly in a patient. A high frequency current generator 30 is connected to an electrode of a catheter or an ablation device 1 through an electrical conductor 29. A wire electrode 12 of an ablation catheter or a medical device 1 is to contact a tissue 25 directly or optionally through a pre-implanted stent 21 when the device is deployed. In the optional case of stent-assisted treatment, the stent is in close contact with the underlying tissue 25. A DIP (dispersive indifferent pad) type pad 32, that contacts the patient, is connected to the Indifferent Electrode Connector on the high frequency generator 30. Therefore, the high frequency current delivery becomes effective when a close circuit from a high frequency generator through a patient and returning to the high frequency current generator is formed. Impedance 33 measured from the tissue contact is to ensure good tissue contact for ablation purposes, otherwise the high frequency power is cut off when the impedance is unreasonably high. A temperature sensor 27 is also used to measure the tissue temperature and is relayed through a temperature sensing wire 28 and a closed-loop temperature controller 34 for controlling the ablative energy delivery. Heat is controlled by the power of the high frequency energy delivered and by the delivery duration.

Figure 2:
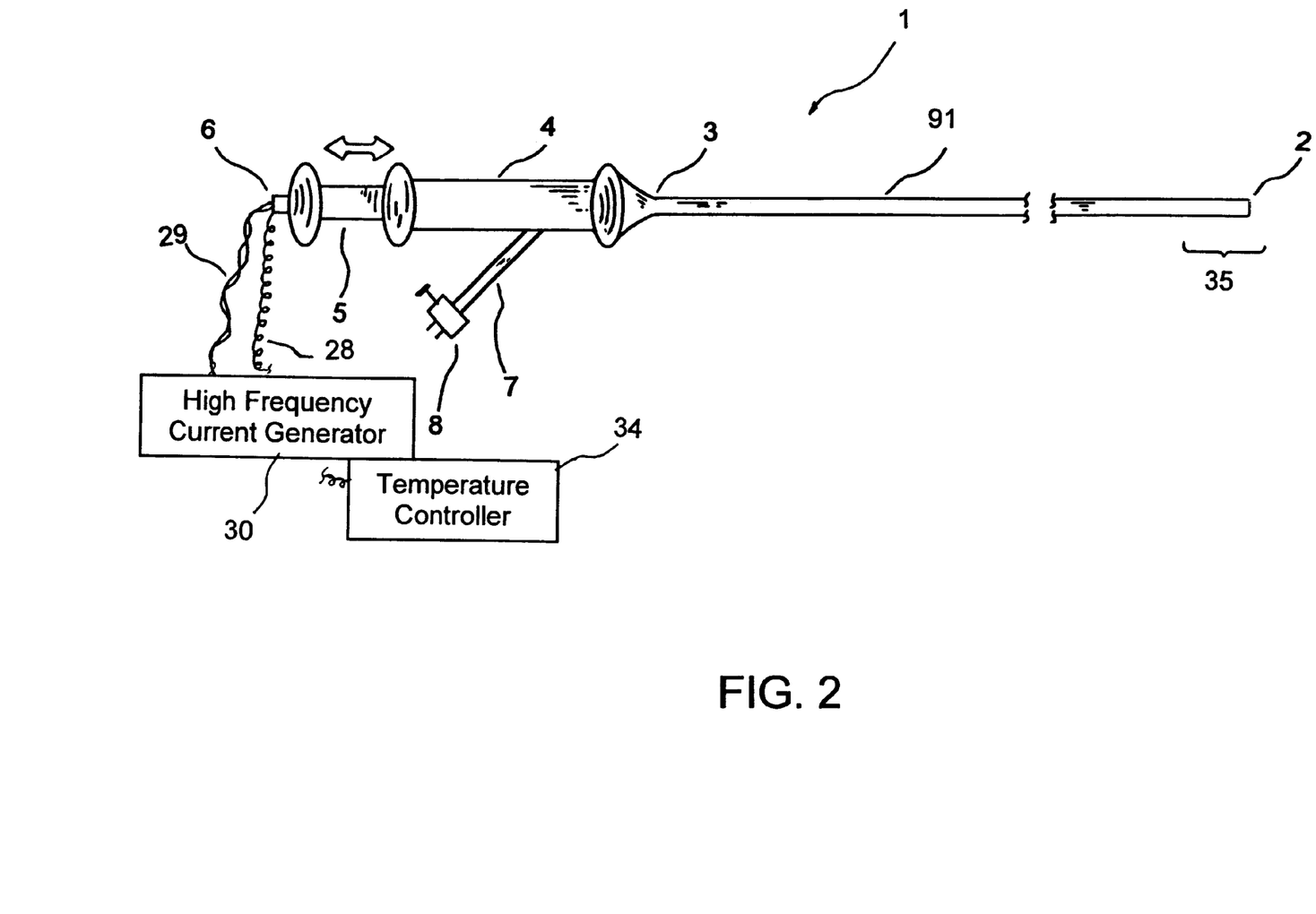
FIG. 2 is an overall view of the medical device having a deployable wire electrode and RF generator, constructed in accordance to the principles of the present invention.

As shown in FIG. 2, the medical device system in the form of an elongate tubular assembly 1 comprises a flexible tubular shaft 91 having a distal section 35, a distal end 2, a proximal end 3, and at least one lumen 10 or 11 extending therebetween, wherein the at least one lumen may have at least one opening at the distal end of the tubular shaft 91. A handle 4 is attached to the proximal end 3 of the tubular shaft, wherein the handle 4 has a cavity. A hollow tubing 7 having a passageway and a locking valve 8 is attached to the handle 4, wherein the passageway is connected to the at least one lumen 11 of the tubular shaft 91. An elongate tubular element is located inside the at least one lumen 10 of the tubular shaft 91, wherein the elongate tubular element comprises a distal end 13 and a proximal end, and wherein the distal end 13 comprises a preshaped spiral wire electrode 12.

In one embodiment, the spiral wire electrode has a plurality of spirals, whereby the diameter of at least one of the next spiral 36 is larger than that of the prior spiral 37. An electrode deployment mechanism 5 is mounted on the handle 4, wherein the electrode deployment mechanism is attached to the proximal end of the elongate tubular element. A high frequency energy generating means 30 is part of the catheter system, wherein the high frequency energy is provided to the spiral wire electrode 12 for therapeutic purposes through the conducting wire 29 and a connector 6 secured at the proximal end of the handle 4. The high frequency current may be selected from the group consisting of radiofrequency current, microwave current and ultrasound current.

Figure 3:
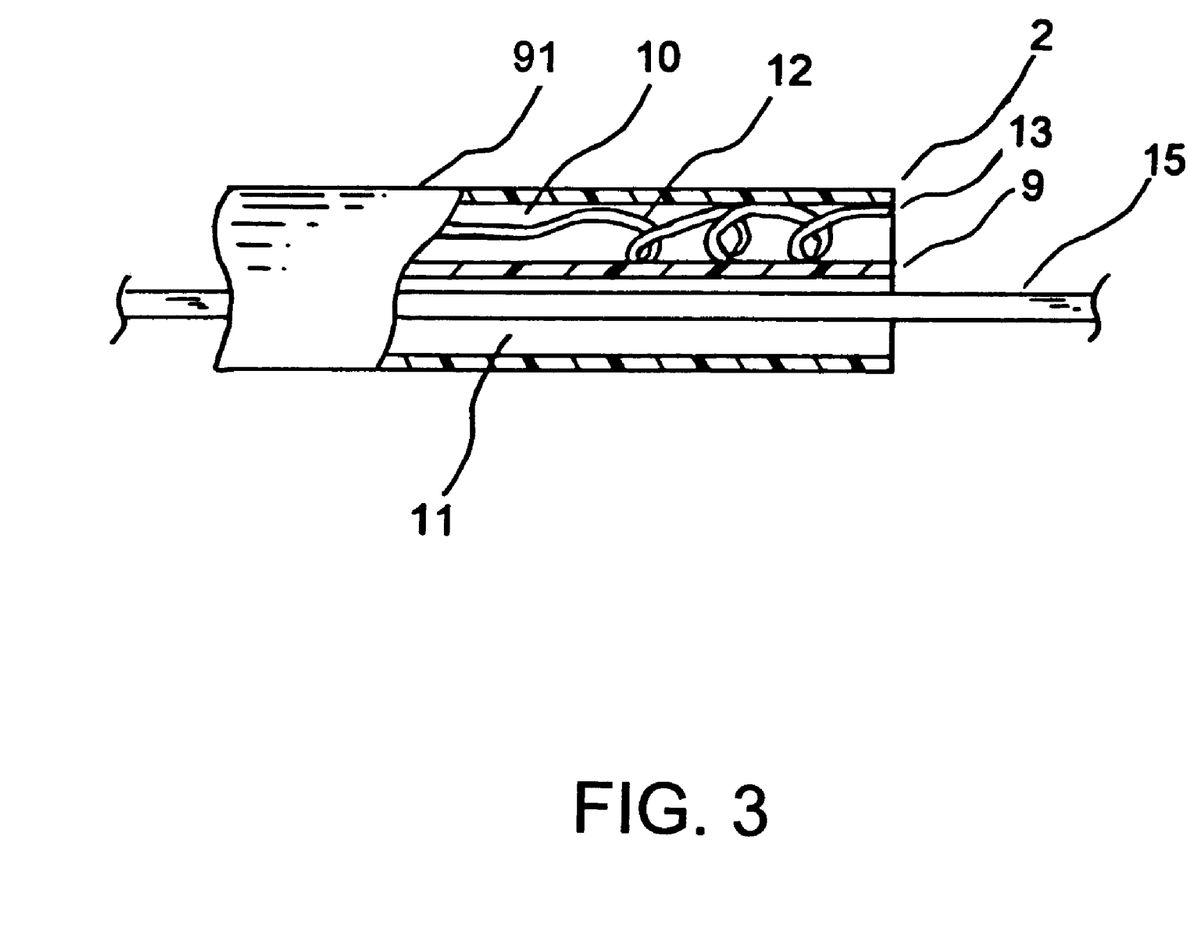
FIG. 3 is a cross-sectional view of the distal end portion of the device, having a deployable wire electrode positioned within a lumen of the tubular shaft, at a non-deployed state.

FIG. 3 shows a cross-sectional view of the distal end portion of the device 1, including a deployable wire electrode 12. Under a non-deployed state, the deployable wire electrode 12 is retracted inside the lumen 10 of the distal end portion 35. The wire end 13 is located just within the distal end 2 of the tubular shaft 91. In one embodiment, the distal end has two lumens 10 and 11. One lumen 10 is used by the deployable wire electrode 12 for treating a tissue. The other lumen 11 could be used to tract a previously inserted guidewire 15 to the lesion site. The device 1 of the present invention may ride on the existing guidewire 15 to the target site 25 for ablation operations.

An insulated electrical conductor 29 or the elongate tubular element itself that may serve as a conducting means passes through the lumen 10 of the shaft 91 and is connected to the wire electrode means 12. The other end of the electrical conductor means is connected to an external high frequency current generator 30.

Figure 4:
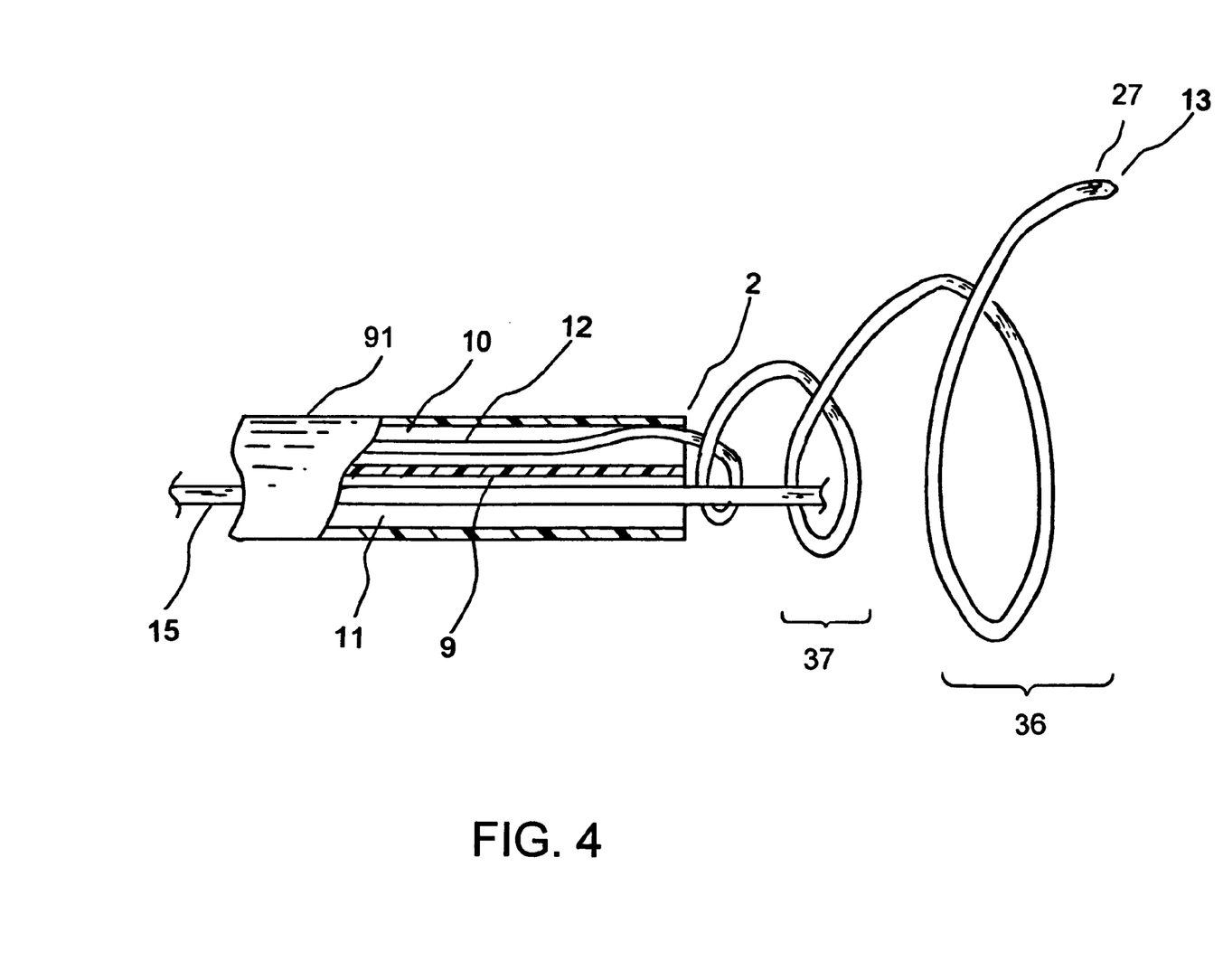
FIG. 4 is a cross-sectional view of the distal end portion of the device, having a deployable wire electrode being deployed to its full extent, at a deployed state.

FIG. 4 shows a cross-sectional view of the distal end portion 35 of the tubular shaft 91 at a deployed state. The deployment operation is initiated at an electrode deployment mechanism 5 that is located at the handle 4. The deployed wire electrode 12 is extendable radially to contact the inside surface of a pre-implanted stent 21, to contact an inner surface of an annular organ structure, or to contact a tissue. This distal portion of the deployed wire electrode and its tissue-contacting surface is made of conductive material, which is connected to the RF energy source through an insulated electrical conductor. Other portion of the tubular shaft and surface of the device is not conductive. In one embodiment, the inner, non-tissue-contacting side of the spiral wire electrode 12 is insulated or coated with an insulation material. The radially extendible spiral wire electrode 12 may be extended radially at least twice the diameter of the tubular shaft 91.

In one embodiment, at least one temperature sensing means 27 is disposed at close proximity of the wire electrode 12. Insulated temperature sensor wire means 28 passes from the temperature sensing means 27, to an external temperature control mechanism 34 through the outlet connector 6. The high frequency energy delivery is controlled by using the measured temperature from the temperature sensing means 27, through a closed-loop temperature control mechanism and/or algorithm. When the measured temperature rises to a preset high-limit point, the temperature control mechanism sends out a signal to cut off the high frequency energy supply. In a similar manner, when the measured temperature drops to a preset low-limit point, the temperature control mechanism sends out a signal to activate the high frequency energy supply.

Figure 5:
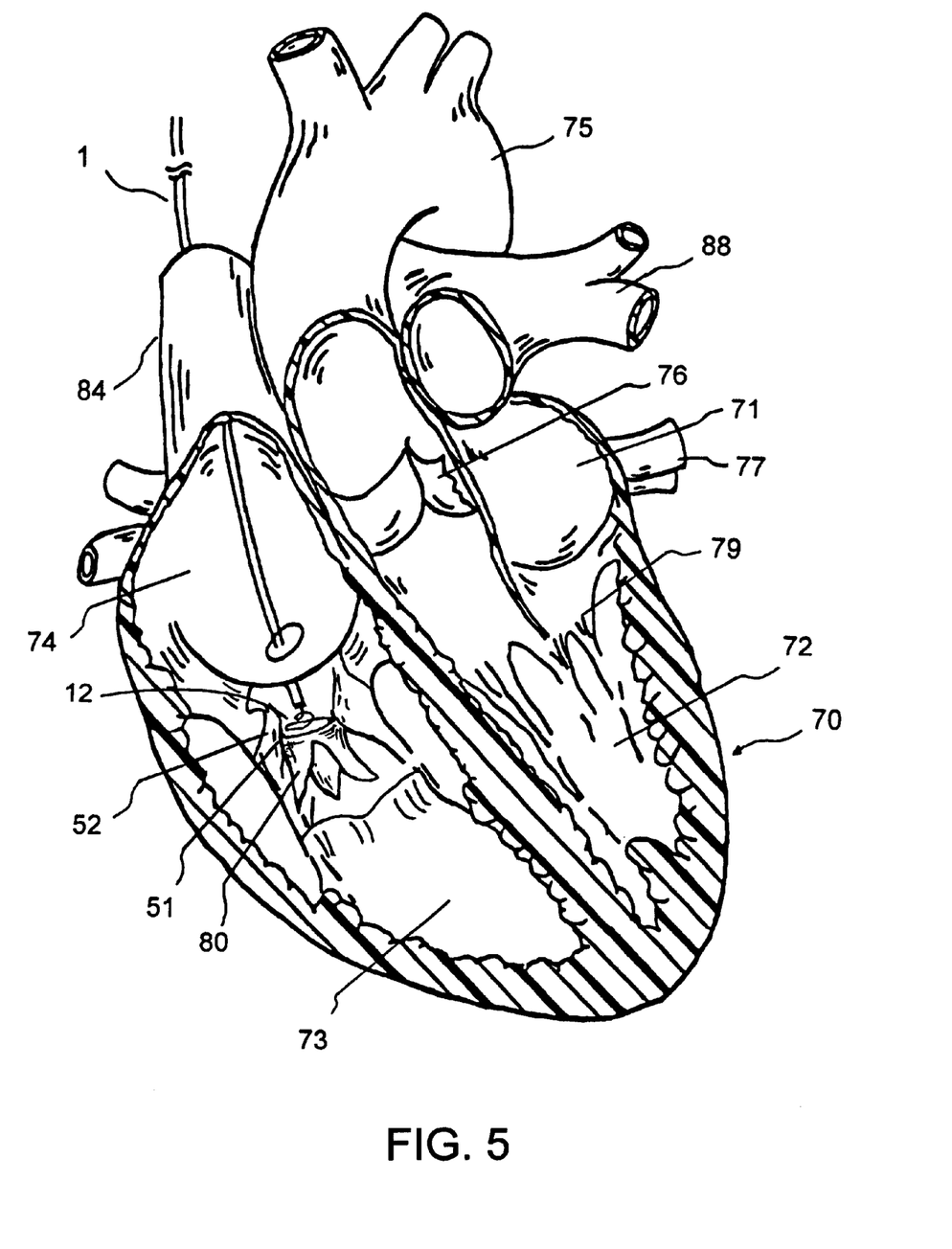
FIG. 5 is a perspective view of a heart tissue being treated by the medical device of the present invention.

FIG. 5 shows a perspective view of a heart tissue being treated by the medical device of the present invention. The heart 70 has a left atrium 71, a left ventricle 72, a right ventricle 73, and a right atrium 74. Aorta 75 connects with the left ventricle 72 and contains an aorta valve 76. Pulmonary artery 77 connects with the right ventricle 73 through a pulmonary valve. Left atrium 71 communicates with the left ventricle 72 through a mitral valve 79. The right atrium 74 communicates with the right ventricle 73 through a tricuspid valve 80. Oxygenated blood is returned to the heat 70 via pulmonary veins 88. In a perspective illustration, a catheter is inserted into the right atrium 74 and is positioned on the inner wall 51 of the tricuspid valve 80. The leaflets of the tricuspid valve 80 open toward the ventricle side. Blood returned from the superior vena cava 84 and the inferior vena cava flows into the right atrium 74. Subsequently, blood flows from the right atrium 74 to the right ventricle 73 through the tricuspid valve 80. The very distal spiral 36 of the spiral wire electrode 12 is to contact the tissue of an annular organ structure 52. Therefore, the spiral wire electrode 12 when deployed from the catheter shaft 91 from the atrial side does not interfere with the leaflet movement during the proposed minimum invasive thermal therapy of the invention.

Figure 6:
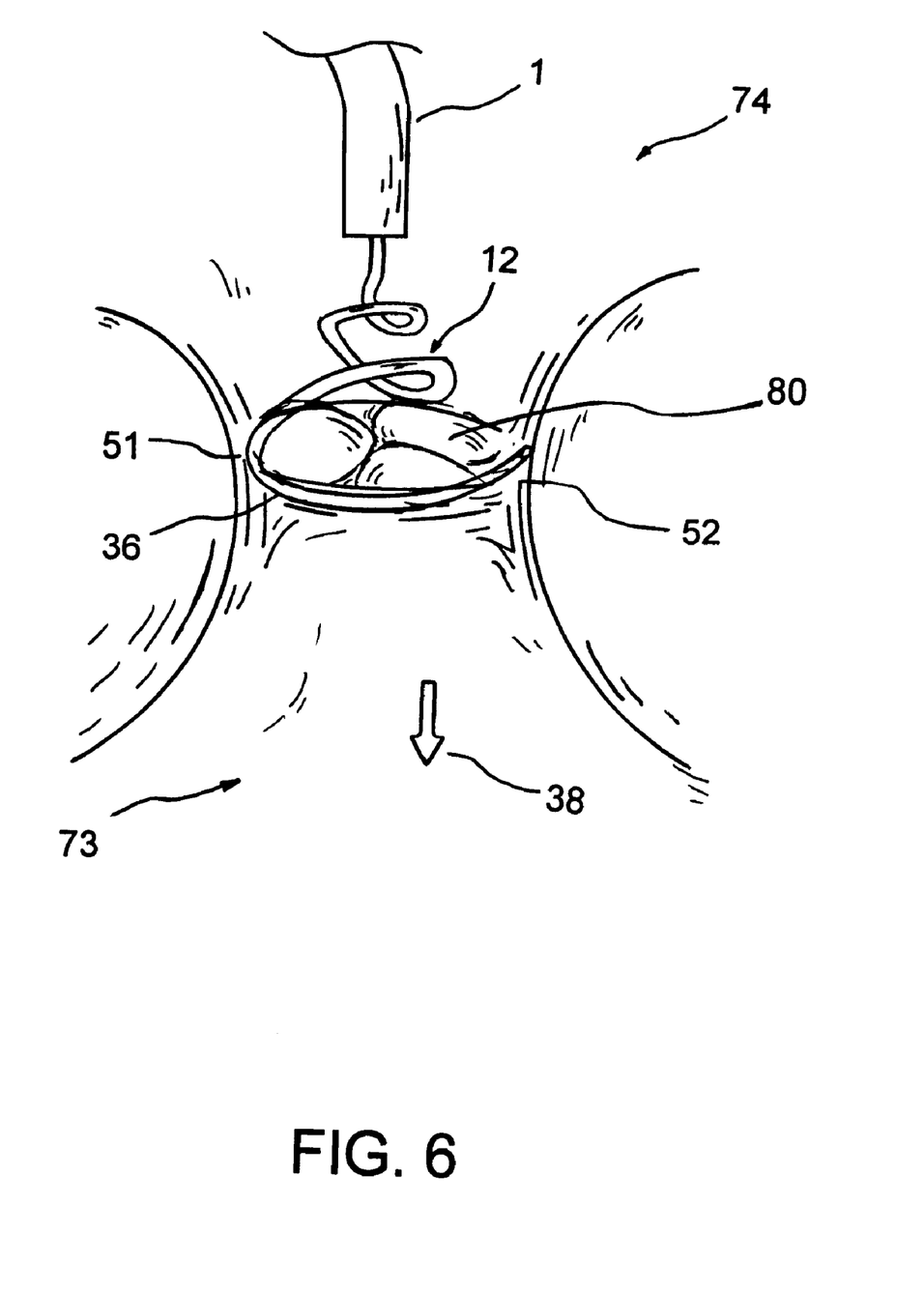
FIG. 6 is a simulated view of the catheter system of the present invention in contact with the tissue of an annular organ structure.

FIG. 6 shows a simulated view of the catheter system of the present invention in contact with the tissue of an annular organ structure 52. For illustration purposes, a catheter 1 having an electrode 12 at a distal section of a catheter shaft 91 is inserted into the right atrium 74. The bloodstream (as shown by an arrow 38) flows from the right atrium 74 through a tricuspid valve 80 to the right ventricle 73. The very distal spiral 36 of the spiral electrode 12 contacts the inner wall 51 of an annular organ structure 52. High frequency energy may be applied to the tissue of the annular organ structure through the contacting spiral electrode 12 of the present invention.

During procedures, the ablation device is inserted into the body of a patient through natural opening or a surgical hole. For one embodiment, a method for operating a catheter system for treating a valvular annulus, the method comprises the steps of (a) percutaneously introducing the catheter system through a blood vessel to a valvular annulus, the catheter system comprising a flexible tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of at least one of a next spiral is larger than that of a prior spiral; an electrode deployment mechanism mounted at the handle, wherein the electrode deployment mechanism is attached to the proximal end of the elongate tubular element; and (b) deploying the elongate tubular element to radially extend the spiral wire electrode, adapted to contact a tissue of the valvular annulus for treatment.

The method may further comprise a step of applying high frequency current to the spiral wire electrode to effect treating the valvular annulus, wherein the catheter system further comprises a high frequency current generator having an electrical conductor means for transmitting high frequency current to said spiral wire electrode. The high frequency current may be selected from the group consisting of radiofrequency current, microwave current and ultrasound current.

The catheter system of the present invention may further comprise at least one temperature sensor disposed at close proximity of the spiral wire electrode for measuring tissue temperature, and comprise temperature control means for controlling the high frequency current transmission to the spiral wire electrode by receiving a measured temperature from the at least one temperature sensor. Furthermore, the valvular annulus may be selected from the group consisting of the valvular annulus of a mitral valve, a tricuspid valve, a pulmonary valve, an aortic valve, and a venous valve. The material for the spiral wire electrode may be selected from the group consisting of platinum, iridium, gold, silver, stainless steel, tungsten, Nitinol, and an alloy of their mixtures.

As an alternative illustration, a method for operating a catheter system for treating a tissue of a valvular organ structure, the method comprises the steps of (a) percutaneously introducing the catheter system through a blood vessel to the tissue of the valvular organ structure, the catheter system comprising a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of at least one of a next spiral is larger than that of a prior spiral; an electrode deployment mechanism mounted on the handle, wherein the electrode deployment mechanism is attached to the proximal end of the elongate tubular element; and a high frequency current generator having an electrical conductor means for transmitting high frequency current to said spiral wire electrode; (b) deploying the elongate tubular element to radially extend the spiral wire electrode, adapted to contact the tissue of the valvular organ structure; and (c) applying high frequency current through the electrical conductor means to the spiral wire electrode for treatment of the valvular organ structure. The tissue may be selected from the group consisting of the tissue of a valvular annulus, a chordae tendinae, a heart valve leaflet, a venous valve leaflet, and papillary muscles.

As still another alternate illustration, a method for operating an ablation catheter system for treating a tissue of a valvular organ structure of a patient, the method comprises the steps of (a) percutaneously introducing the catheter system through a blood vessel of the patient to the tissue of the valvular organ structure, the catheter system comprising a flexible tubular shaft having a distal section, a distal end, a proximal end, and at least one lumen extending therebetween; a deployable elongate tubular element located inside the at least one lumen of the tubular shaft, wherein the elongate tubular element comprises a distal end and a proximal end; an electrode means for contacting the tissue of the valvular organ structure mounted at the distal end of the deployable elongate tubular element; and a radiofrequency current generator having an electrical conductor means for transmitting radiofrequency current to said electrode means; (b) deploying the elongate tubular element out of the distal end of the flexible tubular shaft to contact the tissue of the valvular organ structure; and (c) applying radiofrequency current through the electrical conductor means to the electrode means for treating the tissue of the valvular organ structure. The tissue may be selected from the group consisting of a valvular annulus, a chordae tendinae, a heart valve leaflet, a venous valve leaflet, and papillary muscles.

In one embodiment, the external RF energy generator has the capability to supply RF energy by controlling the time, power, and temperature through an optional separate closed-loop temperature control means. The patient is connected to the RF generator means through a DIP electrode to form a closed-loop current system. Therefore, RF energy is applied and delivered to the targeted tissue, through the electrode means of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode and by applying the pressure therapy, the atherosclerosis can be treated.

From the foregoing description, it should now be appreciated that a medical device system for the tubular organs, atherosclerosis, and the treatment of annular organ structure tissues such as a valvular annulus, a chordae tendinae, a heart valve leaflet, a venous valve leaflet, and papillary muscles, comprising a suitable energy source has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for operating a catheter system for treating a valvular annulus, the method comprising the steps of:
   (a) percutaneously introducing the catheter system through a blood vessel to a valvular annulus, the catheter system comprising a flexible tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of at least one of a next spiral is larger than that of a prior spiral; an electrode deployment mechanism mounted at the handle, wherein the electrode deployment mechanism is attached to the proximal end of the elongate tubular element; and
   (b) deploying the elongate tubular element to radially extend the spiral wire electrode, adapted to contact a tissue of the valvular annulus for treatment.

2. A method for operating a catheter system for treating a valvular annulus as in claim 1, the method further comprising a step of applying high frequency current to the spiral wire electrode to effect treating the valvular annulus, wherein the catheter system further comprises a high frequency current generator having an electrical conductor means for transmitting high frequency current to said spiral wire electrode.

3. A method for operating a catheter system for treating a valvular annulus as in claim 1, wherein the catheter system further comprises at least one temperature sensor disposed at close proximity of the spiral wire electrode for measuring tissue temperature.

4. A method for operating a catheter system for treating a valvular annulus as in claim 3, wherein the catheter system further comprises temperature control means for controlling the high frequency current transmission to the spiral wire electrode by receiving a measured temperature from the at least one temperature sensor.

5. A method for operating a catheter system for treating a valvular annulus of claim 1, wherein the valvular annulus is selected from the group consisting of the valvular annulus of a mitral valve, a tricuspid valve, a pulmonary valve, an aortic valve, and a venous valve.

6. A method for operating a catheter system for treating a valvular annulus of claim 2, wherein the high frequency current is selected from the group consisting of radiofrequency current, microwave current and ultrasonic frequency current.

7. A method for operating a catheter system for treating a valvular annulus of claim 1, wherein the inner, non-tissue contacting side of the spiral wire electrode is insulated.

8. A method for operating a catheter system for treating a valvular annulus of claim 1, wherein the material for the spiral wire electrode is selected from the group consisting of platinum, iridium, gold, silver, stainless steel, tungsten, Nitinol, and an alloy of their mixtures.

9. A method for operating a catheter system for treating a valvular annulus of claim 1, wherein the radially extendible spiral wire electrode is extended radially and penetrates into a tissue of the valvular annulus.

10. A method for operating a catheter system for treating a valvular annulus of claim 1, wherein the catheter system further comprises a steering mechanism at the handle for controlling deflection of the distal section of the flexible tubular shaft.

11. A method for operating a catheter system for treating a valvular annulus of claim 1, wherein a shape of at least one of the plurality of spirals is selected from the group consisting of a circular shape, a D-shape, a kidney shape, and an oval shape.

12. A method for operating a catheter system for treating a tissue of a valvular organ structure, the method comprising the steps of:
   (a) percutaneously introducing the catheter system through a blood vessel to the tissue of the valvular organ structure, the catheter system comprising a tubular shaft having a distal section, a distal end, a proximal end, and at least one lumen extending therebetween, wherein the at least one lumen has at least one opening at the distal end of the tubular shaft; a handle attached to the proximal end of the tubular shaft, wherein the handle has a cavity; a hollow tubing having a passageway and a locking valve attached to the handle, wherein the passageway is connected to the at least one lumen of the tubular shaft; an elongate tubular element located inside the at least one lumen of the tubular shaft, wherein the elongate tubular element comprises a distal end and a proximal end, and wherein the distal end comprises a preshaped wire electrode having a plurality of spirals, wherein the diameter of at least one of a next spiral is larger than that of a prior spiral; an electrode deployment mechanism mounted on the handle, wherein the electrode deployment mechanism is attached to the proximal end of the elongate tubular element; and a high frequency current generator having an electrical conductor means for transmitting high frequency current to said spiral wire electrode;
   (b) deploying the elongate tubular element to radially extend the spiral wire electrode, adapted to contact the tissue of the valvular organ structure; and
   (c) applying high frequency current through the electrical conductor means to the spiral wire electrode for treatment of the valvular organ structure.

13. A method for operating a catheter system for treating a tissue of a valvular organ structure as in claim 12, wherein the tissue is selected from the group consisting of the tissue of a valvular annulus, a chordae tendinae, a heart valve leaflet, a venous valve leaflet, and papillary muscles.

14. A method for operating a catheter system for treating a tissue of a valvular organ structure as in claim 12, wherein the catheter system further comprises at least one temperature sensor disposed at close proximity of the spiral wire electrode for measuring tissue temperature.

15. A method for operating a catheter system for treating a tissue of a valvular organ structure as in claim 14, wherein the catheter system further comprises a temperature control means for controlling the high frequency current transmission to the spiral wire electrode by receiving a measured temperature from the at least one temperature sensor.

16. A method for operating a catheter system for treating a tissue of a valvular organ structure as in claim 12, wherein the high frequency current is selected from the group consisting of radiofrequency current, microwave current and ultrasound current.

17. A method for operating a catheter system for treating a tissue of a valvular organ structure as in claim 12, wherein the radially extendible spiral wire electrode is extended radially and penetrates into the tissue of said valvular organ structure.

18. A method for operating a catheter system for treating a tissue of a valvular organ structure as in claim 12, wherein the catheter system further comprises a steering mechanism at the handle for controlling deflection of the distal section of the tubular shaft.

* * * * *